US012378294B2

(12) United States Patent
Steiness

(10) Patent No.: US 12,378,294 B2
(45) Date of Patent: Aug. 5, 2025

(54) IL-4 DERIVED PEPTIDES FOR USE IN THE TREATMENT OF OBESITY

(71) Applicant: SERODUS APS, Copenhagen N (DK)

(72) Inventor: Eva Steiness, Hellerup (DK)

(73) Assignee: SERODUS APS, Copenhagen N (DK)

( * ) Notice: Subject to any disclaimer, the term of this patent is extended or adjusted under 35 U.S.C. 154(b) by 0 days.

(21) Appl. No.: 18/720,291

(22) PCT Filed: Jan. 4, 2023

(86) PCT No.: PCT/EP2023/050109
§ 371 (c)(1),
(2) Date: Jun. 14, 2024

(87) PCT Pub. No.: WO2023/131619
PCT Pub. Date: Jul. 13, 2023

(65) Prior Publication Data
US 2025/0059248 A1    Feb. 20, 2025

(30) Foreign Application Priority Data
Jan. 5, 2022 (EP) .................................. 22150293

(51) Int. Cl.
*C07K 14/54* (2006.01)
*A61P 3/04* (2006.01)
*A61K 38/00* (2006.01)

(52) U.S. Cl.
CPC ............ *C07K 14/5406* (2013.01); *A61P 3/04* (2018.01); *A61K 38/00* (2013.01)

(58) Field of Classification Search
CPC ........ C07K 14/5406; A61P 3/04; A61K 38/00
See application file for complete search history.

(56) References Cited

U.S. PATENT DOCUMENTS

2011/0300148 A1    12/2011    Bock et al.

FOREIGN PATENT DOCUMENTS

WO    2010/054667    5/2010

OTHER PUBLICATIONS

Shiau Ming-Yuh et al, "Mechanism of Interleukin-4 Reducing Lipid Deposit by Regulating Hormone-Sensitive Lipase", vol. 9, No. 1, doi:10.1038/s41598-019-47908-9, (Dec. 1, 2019), p. 11974, Scientific Reports, URL: https://www.nature.com/articles/s41598-019-47908-9.pdf, XP055927143 [A] 1-8 * the whole document + DOI: http://dx.doi.org/10.1038/s41598-019-47908-9.
Klementiev Boris et al, "Antiinflammatory properties of a peptide derived from interleukin-4", US, vol. 64, No. 1, doi:10.1016/j.cyto.2013.07.016, ISSN 1043-4666, (Oct. 1, 2013), pp. 112-121, Cytokine, URL: https://www.sciencedirect.com/science/article/pii/S1043466613006315/pdfft?md5=8d8b5685f12b91b18cc362d9f3339942&pid=1-s2.0-S1043466613006315-main.pdf, XP055927157 [ID] 1-8 * p. 115 * DOI: http://dx.doi.org/10.1016/j.cyto.2013.07.016.
Adv Drug Deliv Rev., (2013), vol. 65, No. 10, pp. 1357-1369.
Proc. Natl. Acad. Sci. USA, (Aug. 1988), vol. 85, pp. 5409-5413
Tam, J P. "Synthetic peptide vaccine design: synthesis and properties of a high-density multiple antigenic peptide system." Proceedings of the National Academy of Sciences of the United States of America vol. 85,15 (1988): 5409-13. doi:10.1073/pnas.85.15.5409.
Abdelaal M. et al., "Morbidity and mortality associated with obesity", Ann Transl Med, (Apr. 2017). vol. 5, No. 7, pp. 1-12, 2017.
Roglic, G.: "World Health Organization", Global Report on Diabetes, 2016.

*Primary Examiner* — Gyan Chandra
(74) *Attorney, Agent, or Firm* — DUANE MORRIS LLP; Gregory M. Lefkowitz; Brandon A. Chan

(57) ABSTRACT

The present disclosure relates to peptides derived from interleukin-4 (IL-4) for the treatment of obesity.

2 Claims, 2 Drawing Sheets

Specification includes a Sequence Listing.

IL-4 DERIVED PEPTIDES FOR USE IN THE TREATMENT OF OBESITY

CROSS-REFERENCE TO RELATED APPLICATIONS

This application is a § 371 national stage entry of International Application No. PCT/EP2023/050109, filed on Jan. 4, 2023, which claims priority to European Patent Application Nos. 22150293.3, filed on Jan. 5, 2022, the entire contents of which are incorporated herein by reference.

SEQUENCE LISTING

The instant application contains a Sequence Listing which has been submitted electronically in a computer readable Sequence Listing XML format and is hereby incorporated by reference in its entirety. Said computer readable Sequence Listing in XML format was created on Jun. 12, 2024, is named F9057-38201_Sequence_Listing.xml and is 5000 bytes in size.

TECHNICAL FIELD

The present disclosure relates to peptides derived from IL-4 for the treatment of obesity. In particular, the present disclosure relates to peptides comprising the amino acid sequence of SEQ ID NO:1 or a variant thereof for use in the treatment of obesity.

BACKGROUND

Overweight and obesity are defined as abnormal or excessive fat accumulation that presents a risk to health. Body mass index (BMI) is calculated based on body weight and height. A BMI over 25 is considered as overweight, and over 30 as obese. Obesity has epidemic dimensions and has in the past 50 years reached pandemic levels. Worldwide obesity has nearly tripled since 1975. In 2016, more than 1.9 billion adults, 18 years and older, were overweight. Of these over 650 million were obese. Over 340 million children and adolescents aged 5-19 were overweight or obese in 2016 (Roglic, G. 2016).

Both overweight and obesity are systemic diseases which are associated with the leading causes of morbidity and death in the United States, including type 2 diabetes, heart disease, stroke, and some types of cancer (Roglic, G. 2016). Obesity is thus a serious condition because it is also associated with poorer mental health outcomes, reduced quality of life, and contributes to a decline in life expectancy (Abdelaal 2017).

Several medicaments have been approved for the treatment of obesity. One example is Semaglutide sold under the trade name Wegovy. Semaglutide is a glucagon-like peptide-1 (GLP-1) agonist which was originally developed and approved for the treatment of type 2 diabetes. The most noteworthy effects of GLP-1 agonists are their ability to promote insulin secretion in a glucose-dependent manner by binding to GLP-1 receptors expressed on the pancreatic β cells. Almost as importantly, GLP-1 agonists have been shown to inhibit glucagon secretion at glucose levels above fasting levels. Critically, this does not affect the glucagon response to hypoglycemia, making GLP-1 agonists a safe anti-diabetic drug with very low incidence of hypoglycemia compared to insulin.

In June 2021, Semaglutide was approved by the FDA for chronic weight management in adults with obesity or overweight with at least one weight-related condition (such as high blood pressure, type 2 diabetes, or high cholesterol). As an anti-obesity drug, GLP-1 agonists work by binding to GLP-1 receptors in hypothalamus thereby suppressing appetite. Furthermore, GLP-1 agonists bind to GLP-1 receptors in the stomach, inhibiting gastric emptying, acid secretion, and motility, which collectively promote satiety. Consequently, diabetic subjects treated with GLP-1 receptor agonists often also experience a beneficial weight loss in addition to a control of their blood sugar levels. However, there is still a need in the art for new and more effective treatments of obesity.

Human interleukin-4 (IL-4) is an anti-inflammatory cytokine with the amino acid sequence (including signal peptide i.e. amino acid $AA_{1-24}$): MGLTSQLLPP LFFLLACAGN FVHGHKCDIT LQEIIKTLNS LTEQKTLCTE LTVTDI-FAAS KNTTEKETFC RAATVLRQFY SHHEKDTRCL GATAQQFHRH KQLIRFLKRL DRNLWGLAGL NSCPVKEANQ STLENFLERL KTIMREKYSK CSS (UniProtKB-P05112; SEQ ID NO:3).

Mature IL-4 has 129 amino acid residues and contains three intramolecular disulfide bonds (Cys3-Cys127; Cys46-Cys99; Cys24-Cys65) with the amino acid sequence: HKCDITLQEI IKTLNSLTEQ KTLCTELTVT DIFAASKNTT EKETFCRAAT VLRQFYSHHE KDTR-CLGATA QQFHRHKQLI RFLKRLDRNL WGLAGLN-SCP VKEANQSTLE NFLERLKTIM REKYSKCSS (SEQ ID NO:4).

Like other cytokines, IL-4 exerts its biological activity by binding to receptors on the cell surface. Two receptor types for IL-4 are known and denoted type I IL-4R and type II IL-4R. The type I IL-4R is composed of two components; the IL-4Rα chain and the IL-2Rγ ($γ_c$) chain, whereas the type II IL-4R is composed of IL-4Rα and the IL-13α1 chain. IL-4 has many biological roles, including the stimulation of activated B cell and T cell proliferation, and the differentiation of B cells into plasma cells. The presence of IL-4 in extravascular tissues promotes alternative activation of macrophages into M2 cells and inhibits classical activation of macrophages into M1 cells resulting in a diminution of pathological inflammation. IL-4 is mainly secreted by CD4+ T-cells (Th2 cells) which control the concert of specific cytokine inhibitors and soluble cytokine receptors to regulate the human immune response and serve a critical role in the pathogenesis of acute and chronic inflammation by maintaining a proper balance between pro- and anti-inflammatory activities. Thus, modulation of IL-4 signaling has been heavily investigated in autoimmune and inflammatory diseases. Recently, IL-4 was shown to promote lipolysis through enhancing hormone-sensitive lipase (HSL) activity (see Scientific Reports, 2019 9:11974).

Small peptides fragments derived from IL-4, acting as IL-4 mimetics, have previously shown to inhibit TNF-α release from macrophages and to induce a neuritogenic response from primary neurons (see WO2010/054667). One such example is the peptide having the amino acid sequence AQFHRHKQLIRFLKRA (SEQ ID NO:1). This peptide is capable of binding to the IL-4 receptors and inhibiting macrophage activation, thereby preventing the onset of inflammatory responses, and has therefore been proposed to be useful in a number of inflammatory and autoimmune diseases such as rheumatoid arthritis, Multiple sclerosis, Alzheimer's disease, Parkinson's disease, and Huntington's disease.

SUMMARY

The present invention relates to the surprising observation that mice administered a peptide comprising SEQ ID NO:1

(i.e. the treatment group) were less susceptible to gain weight compared to the placebo group. Thus, the present invention relates to the realization that peptides derived from IL-4 and acting as IL-4 mimetics may be used in the treatment of obesity albeit such peptides have previously only been associated with anti-inflammatory effects. Thus, peptide fragments derived from IL-4 and acting as IL-4 mimetics may hold promising potential as a new generation of anti-obesity drugs with a novel mode of action as the peptide fragment of SEQ ID NO:1 has been shown to be a high affinity partial agonist on type I IL-4R and an antagonist on type II IL-4R (Klementiv 2013).

In a first aspect, the present disclosure relates to a peptide or a pharmaceutically acceptable salt thereof for use in the treatment of obesity, wherein said peptide comprises 13 to 19 amino acid residues, and further wherein said peptide comprises a fragment with the amino acid sequence AQFHRHKQLIRFLKRA (SEQ ID NO:1), or a variant of AQFHRHKQLIRFLKRA (SEQ ID NO:1) having one, two, or three amino acid substitutions and/or deletions.

In a second aspect, the present disclosure relates to a peptide or a pharmaceutically acceptable salt thereof for use in the treatment of obesity, wherein said peptide comprises two or more covalently linked peptide fragments according to the first aspect.

In a third aspect, the present disclosure relates to a pharmaceutical composition for use in the treatment of obesity, wherein said pharmaceutical composition comprises a peptide according to the first and/or second aspect.

In a fourth aspect, the present disclosure relates to a method for treatment of obesity, the method comprising administering an effective amount of a peptide, or pharmaceutical composition to an individual in need thereof according to any of the aspects and embodiments disclosed herein.

Definitions and Abbreviations

The term "individual" refers to vertebrates, particular members of the mammalian species, preferably primates, including humans. As used herein, 'subject' and 'individual' may be used interchangeably.

An "individual in need thereof" refers to an individual who may benefit from the present disclosure. In one embodiment, the individual in need thereof is an individual being obese (BMI above >30), preferably with at least one weight-related condition (such as high blood pressure, type 2 diabetes, or high cholesterol). In another embodiment, the individual in need thereof is an individual being overweight (BMI above >25), preferably with at least one weight-related condition (such as high blood pressure, type 2 diabetes, or high cholesterol). Therefore, in the present context "obesity" should be understood in a broad sense to include overweight (BMI above >25), preferably with at least one weight-related condition (such as high blood pressure, type 2 diabetes, or high cholesterol).

An "effective amount" of a peptide can be administered in one administration, or through multiple administrations of an amount that totals an effective amount, for instance within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

In the present context when the disclosure refers to a peptide fragment, wherein a number of contiguous amino acid residues are derived from the amino acid region, e.g., $AA_{68}$-$AA_{97}$ of interleukin-4 (SEQ ID NO:4), it should be understood as a small stretch of amino acids (i.e. a contiguous sequence) selected from the respective region of interleukin-4 (SEQ ID NO:4). Thus, the cytokine IL-4 (SEQ ID NO:4) does not form part of the invention. As a non-limiting example, e.g., a peptide fragment comprising 16 contiguous amino acid residues derived from the amino acid region $AA_{68}$-$AA_{89}$ of interleukin-4 (SEQ ID NO:4) can be obtained from the contiguous sequence highlighted in bold below.

(SEQ ID NO: 4)
HKCDITLQEI IKTLNSLTEQ KTLCTELTVT DIFAASKNTT

EKETFCRAAT VLRQFYSHHE KDTRCLGATA QQFHRHKQLI

RFLKRLDRNL WGLAGLNSCP VKEANQSTLE NFLERLKTIM

REKYSKCSS.

Thus, 16 contiguous amino acid residues derived from the amino acid region $AA_{68}$-$AA_{89}$ of interleukin-4 (SEQ ID NO:4) include the fragments/sequences ATAQQFHRHKQLIRFL; TAQQFHRHKQLIRFLK; AQQFHRHKQLIRFLKR, QQFHRHKQLIRFLKRL, QFHRHKQLIRFLKRLD, FHRHKQLIRFLKRLDR, HRHKQLI RFLKRLDRN, and RHKQLI RFLKRLDRNL. The peptides may be a variant of the fragments/sequences derived from interleukin-4 (SEQ ID NO:4). As a non-limiting example, AQFHRHKQLIRFLKRA (SEQ ID NO:1) is a variant of the fragment/sequence QQFHRHKQLIRFLKRL, wherein the terminal amino acids Q and L have been substituted with A (i.e. AQFHRHKQLIRFLKRA (SEQ ID NO:1) has two amino acid substitutions). Thus, in the present context when the disclosure refers to a peptide that e.g. comprises a fragment of 13 to 19 contiguous amino acid residues derived from the amino acid region $AA_{68}$-$AA_{97}$ of interleukin-4 (SEQ ID NO:4), it should be understood that the number of contiguous amino acids cannot be below 13 and cannot exceed 19 amino acids in a single amino acid stretch (i.e. in a fragment, not taking any linker into account if present), but that the peptide may comprise more than one such fragment linked through a linker (spacer). As a non-limiting example, the peptide below of Formula (I) comprises two peptide fragments of each 16 contiguous amino acids that are linked via a linker at their C-terminal.

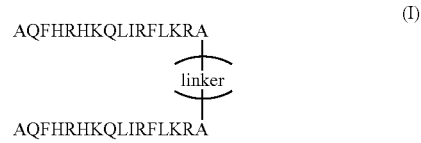

(I)

The peptide fragment(s) may also be lipidated to alter the pharmacokinetic properties of the peptides.

"Sequence identity" as used herein is the number of amino acid residues which match exactly between two different sequences to be compared. If a variant is 90% identical to a sequence having ten amino acid residues, the variant can differ from the sequence by one amino acid substitution.

The terms "treating", "treatment" and "therapy" as used herein refer equally to curative therapy, prophylactic, preventative or ameliorating therapy. The term includes an approach for obtaining beneficial or desired physiological results, which may be established clinically, such as e.g. weight loss or reduced fat percentage.

The term "covalently linked" should be understood as at least two peptides/fragments according to the disclosure covalently linked to each other through a linker or spacer. The covalently linked peptides may have the same sequence or different sequences. Various type of linkers (spacers) may be used to link the peptides together, e.g. those commonly known in the art for peptide dendrimers, fusion peptides/proteins, or hybrid peptides. E.g. the linker (spacer) may be a peptide linker, e.g. lysine-beta-alanine as illustrated herein, a single amino acid such as lysine, or a small stretch of amino acids (see e.g. Adv Drug Deliv Rev. 2013 Oct. 15; 65 (10): 1357-1369). The linker may also be a non-peptide linker, e.g. PEG chain or a diamine such as ethylene diamine. The skilled person will appreciate that the linker (spacer) used may be changed to other linkers (spacers) without departing from the inventive concept. Most preferably, the peptides/fragments are covalently linked via their N-terminal or C-terminal, most preferably their C-terminal as illustrated herein. Most preferably, the two peptides/fragments are linked by a lysine as illustrated herein. The beta-alanine of the lysine linker part merely acts as a spacer between the Rink linker used in the SPPS to reduce steric hindrance during synthesis. The beta-alanine part may therefore be substituted with other common spacers used in the art of SPPS. Various branched dendrimers based on lysine may be obtained as e.g. described in (Proc. Natl. Acad. Sci. USA, Vol 85, pp. 5409-5413, August 1988). The dimer disclosed herein was found to perform better than the monomer.

The term "variant" means that the peptide sequence may be modified, for example by substitution of one or more of the amino acid residues. Both L-amino acids and D-amino acids may be used as well as unnatural amino acids, preferably L-amino acids are used. In the present context, when referring to a variant having one, two, or three amino acid substitutions and/or deletions, it should be understood that the sum of the substitutions and/or deletions is maximum three. As an example, a variant may e.g. have two substitutions and one deletion (sum=3). Likewise, a variant may have three substitutions and zero deletions (sum=3), or a variant may have three deletions and zero substitutions (sum=3). As an example, it follows that when the present disclosure relates to a peptide for use in the treatment of obesity, wherein said peptide e.g. has 13 amino acid residues and further wherein said peptide comprises a variant of AQFHRHKQLIRFLKRA (SEQ ID NO:1, i.e. 16 amino acids), it must be a variant having three deletions (16×3=13 amino acids). Preferably, a substitution in a variant is a conservative substitution to a conservative amino acid. The groups of conservative amino acids are as the following:
 A, G (neutral, weakly hydrophobic),
 Q, N, S, T (hydrophilic, non-charged)
 E, D (hydrophilic, acidic)
 H, K, R (hydrophilic, basic)
 A, L, P, I, V, M, F, Y, W (hydrophobic, aromatic)
 C (cross-link forming)

Conservative substitutions may be introduced in any position of the peptide for use according to the present disclosure. It may however also be desirable to introduce non-conservative substitutions, in any position of the peptide for use according to the present disclosure.

The peptide sequences of the present disclosure may be prepared by any conventional synthetic methods such as solid phase peptide synthesis (SPPS).

The peptides according to the invention may be in the form of a pharmaceutically acceptable salt. Thus, pharmaceutically acceptable salts are intended to include any salts that are commonly used in formulations of peptides. Such salts include both acid addition salts and basic salts, and examples may be found e.g. in Remington's Pharmaceutical Sciences, 17 th edition.

DETAILED DESCRIPTION

The present invention relates to the surprising finding that small peptide fragments derived from IL-4, more particularly the α-helix C of IL-4, (i.e. IL-4R type I agonists), which have previously only been associated with anti-inflammatory effects, have been found to significantly decrease the body weight in animals upon administration.

Thus, the present disclosure relates to peptides for use in the treatment of obesity, wherein the peptides are an IL-4 receptor type I agonists and, preferably IL-4 receptor type II antagonists.

Mature IL-4 has 129 amino acid residues and contains three intramolecular disulfide bonds (Cys3-Cys127; Cys46-Cys99; Cys24-Cys65). The peptide used in the experimental section herein has the amino acid sequence of AQFHRHKQ-LIRFLKRA (SEQ ID NO: 1) (i.e. a first fragment) covalently linked to another peptide having the amino acid sequence of AQFHRHKQLIRFLKRA (SEQ ID NO: 1) (i.e. a second fragment) through a linker (spacer) (i.e. lysine-beta-alanine). The peptide of SEQ ID NO: 1 is a variant of the peptide derived from the amino acids $AA_{71}$-$AA_{86}$ of SEQ ID NO:4 (IL-4 without signal sequence) (highlighted in bold below).

```
                                          (SEQ ID NO: 4)
HKCDITLQEI IKTLNSLTEQ KTLCTELTVT DIFAASKNTT

EKETFCRAAT VLRQFYSHHE KDTRCLGATA QQFHRHKQLI

RFLKRLDRNL WGLAGLNSCP VKEANQSTLE NFLERLKTIM

REKYSKCSS
```

As can be seen from the alignment of SEQ ID NO:1 with the amino acids $AA_{71}$-$AA_{86}$ of SEQ ID NO:4, SEQ ID NO:1 is a variant of the peptide fragment derived from this region having two amino acid substitutions (highlighted in bold).

```
                                          (SEQ ID NO: 4)
    QQFHRHKQLIRFLKRL AA71-AA86 Of IL-4

(SEQ ID NO: 1)
    AQFHRHKQLIRFLKRA
```

Figure 1A:
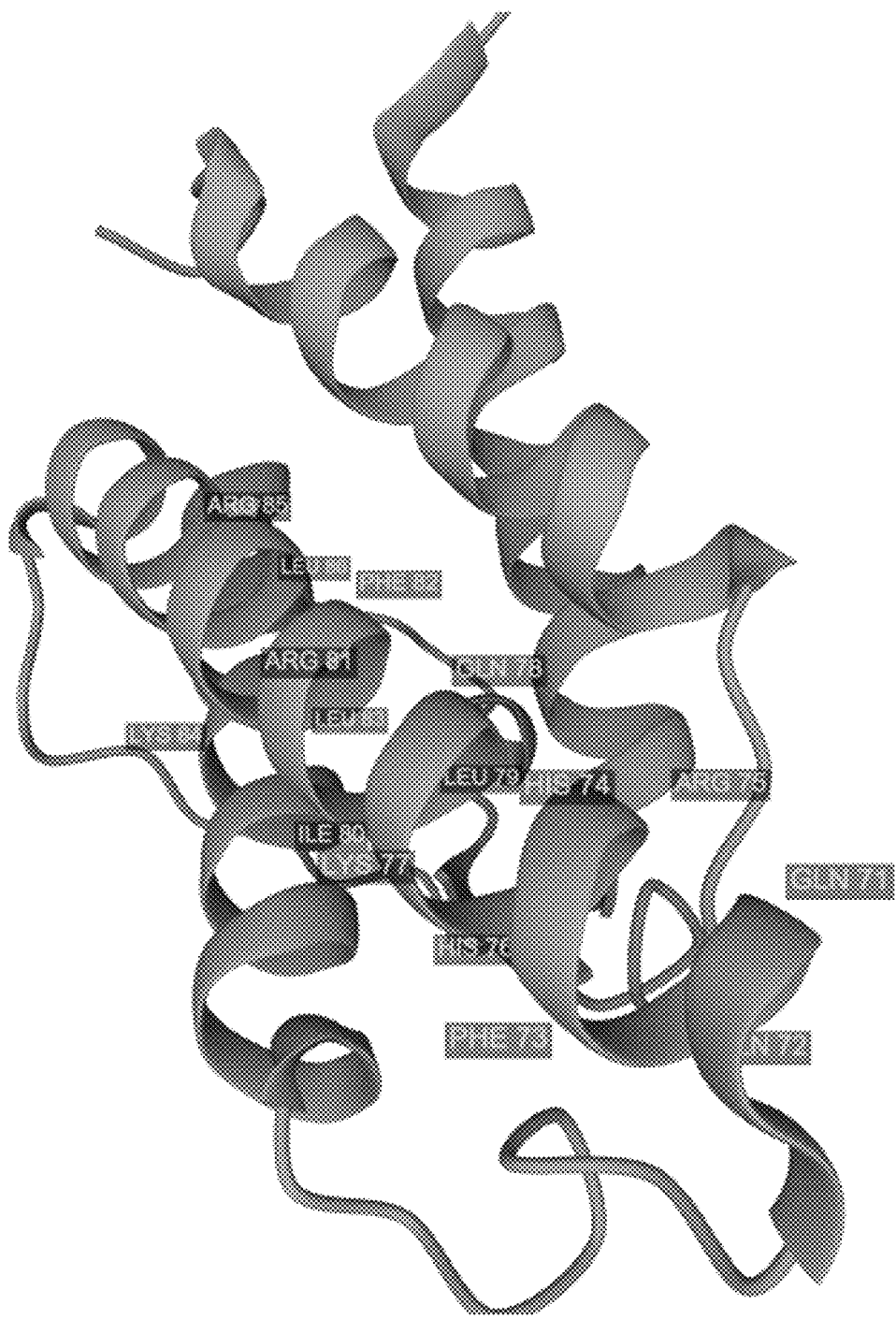
FIGS. 1A and 1B shows the crystal structure of IL-4(PDB identifier: 1 CYL) with the amino acid residues indicated for the region $AA_{71}$-$AA_{86}$ which forms part of the α-helix C ($AA_{71}$-$AA_{94}$).
Figure 1B:
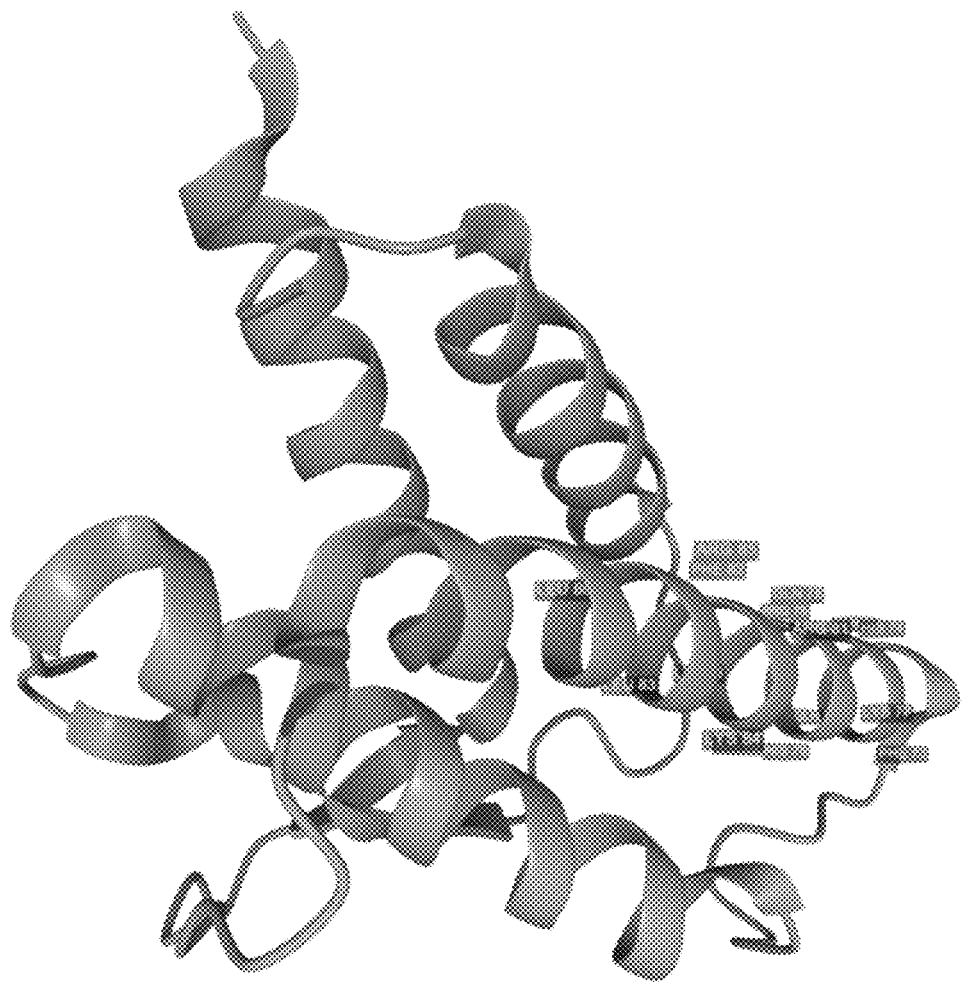

The region $AA_{71}$-$AA_{86}$ of SEQ ID NO:4 forms part of the α-helix C ($AA_{71}$-$AA_{94}$) of IL-4 as shown in the crystal structure in FIG. 1A/B (PDB identifier: 1 CYL). This α-helix C interacts with the ectodomain part of IL-4Rα1 and therefore, peptide fragments derived from the α-helix C ($AA_{71}$-$AA_{94}$) are likely to possess similar binding characteristics and pharmacology as SEQ ID NO:1. In order words peptides derived from the region at or in close proximity to $AA_{71}$-$AA_{94}$, preferably $AA_{71}$-$AA_{86}$ of SEQ ID NO:4, are suitable for use in the treatment of obesity. The peptide fragments derived from the α-helix C ($AA_{71}$-$AA_{94}$) may form an α-helix, at least for part of the amino acid sequence. The tendency of short peptides to form an α-helix may be predicted using software, such as PROTEUS Structure Prediction Server or may be determined experimentally using e.g. X-ray crystallography. As can be seen PROTEUS Structure Prediction Server predicts the amino acids highlighted in bold AQFHRHKQLIRFLKRA (SEQ ID NO:1) to have a high tendency to form an α-helix (confidence score 9 in scale ranging from 0-9, 9 being highest confidence). Thus, most preferably, at least part of the fragments derived from α-helix C ($AA_{71}$-$AA_{94}$) of IL-4 forms an α-helix.

In particular, the present invention relates to the finding that a peptide comprising the fragment with the amino acid sequence AQFHRHKQLIRFLKRA (SEQ ID NO:1) significantly decreases the body weight gain in animals upon administration as shown in the experimental section herein.

Thus, in a first aspect, the present disclosure relates to a peptide for use in the treatment of obesity, wherein said peptide comprises 13 to 19 amino acid residues, and further wherein said peptide comprises a fragment with amino acid sequence AQFHRHKQLIRFLKRA (SEQ ID NO:1), or a variant of AQFHRHKQLIRFLKRA (SEQ ID NO:1) having one, two, or three amino acid substitutions and/or deletions.

In a preferred embodiment, the present disclosure relates to a peptide for use in the treatment of obesity, wherein said peptide comprises 14 to 18 amino acid residues and further wherein said peptide comprises a fragment with amino acid sequence AQFHRHKQLIRFLKRA (SEQ ID NO:1), or a variant of AQFHRHKQLIRFLKRA (SEQ ID NO:1) having one, two, or three amino acid substitutions and/or deletions.

In a more preferred embodiment, the present disclosure relates to a peptide for use in the treatment of obesity, wherein said peptide comprises 15 to 17 amino acid residues, and further wherein said peptide comprises a fragment with the amino acid sequence AQFHRHKQLIRFLKRA (SEQ ID NO:1), or a variant of AQFHRHKQLIRFLKRA (SEQ ID NO:1) having one, two, or three amino acid substitutions and/or deletions.

In an even more preferred embodiment, the present disclosure relates to a peptide for use in the treatment of obesity, wherein said peptide comprises 16 amino acid residues, and further wherein the peptide comprises a fragment with SEQ ID NO:1 (AQFHRHKQLIRFLKRA) or a variant of SEQ ID NO:1 (AQFHRHKQLIRFLKRA) having one, two, or three amino acid substitutions.

In another embodiment, the present invention relates to a peptide or a pharmaceutically acceptable salt thereof for use in the treatment of obesity, wherein the peptide comprises 13 to 19 contiguous amino acid residues derived from the amino acid region $AA_{68}$-$AA_{97}$, preferably $AA_{71}$-$AA_{94}$, more preferably $AA_{71}$-$AA_{89}$, most preferably $AA_{71}$-$AA_{86}$ of interleukin-4 (SEQ ID NO:4), or is a variant thereof having one, two, three, or four amino acid substitutions. In a more preferred embodiment, the peptide has 14 to 18 contiguous amino acid residues derived from the amino acid region $AA_{68}$-$AA_{97}$, preferably $AA_{71}$-$AA_{94}$, preferably $AA_{71}$-$AA_{89}$, most preferably $AA_{71}$-$AA_{86}$, interleukin-4 (SEQ ID NO:4), or is a variant thereof having one, two, three, or four amino acid substitutions. In a more preferred embodiment, the peptide has 15 to 17 contiguous amino acid residues derived from the amino acid region $AA_{68}$-$AA_{97}$, preferably $AA_{71}$-$AA_{94}$, preferably $AA_{71}$-$AA_{89}$, most preferably $AA_{71}$-$AA_{86}$ of interleukin-4 (SEQ ID NO:4), or is a variant thereof having one, two, three, or four amino acid substitutions. In an even more preferred embodiment, the peptide has 16 contiguous amino acid residues derived from the amino acid region $AA_{68}$-$AA_{97}$, preferably $AA_{71}$-$AA_{94}$, more preferably $AA_{71}$-$AA_{89}$, most preferably $AA_{71}$-$AA_{86}$ of interleukin-4 (SEQ ID NO:4), or is a variant thereof having one, two, three, or four amino acid substitutions. In the above-mentioned embodiments, it is highly preferred that the peptide comprises the amino acid sequence AQFHRHKQLIRFLKRA (SEQ ID NO:1), or a variant of AQFHRHKQLIRFLKRA (SEQ ID NO:1) having one or two substitutions.

In any of the above-mentioned embodiments, the variant preferably has two amino acid substitutions and/or deletions, even more preferably one amino acid substitution or deletion.

The peptides for use according to the disclosure may be amidated at the C-terminal (—$CONH_2$), have a free carboxylic acid (—COOH), or another post-translational modification, such as a methyl ester (—COOMe). The peptides according to the present invention may have a free amine (—$NH_2$), be N-acylated (—NHCOR), N-methylated (—$NHCH_3$ or —$N(CH_3)_2$) or deaminated at the N-terminal. The peptides may also be lipidated, e.g. at the N-terminal and/or at one or more lysine residue(s), in order to alter the PK properties of the peptides.

Thus, in an embodiment of the present disclosure, the C-terminal amino acid exists as the free carboxylic acid ("—COOH"). In another embodiment, the C-terminal amino acid is an amidated derivative ("—$CONH_2$"). In another embodiment, the N-terminal amino acid comprises a free amino-group ("$NH_2$"). In another embodiment, the N-terminal amino acid is the acetylated derivative ($COCH_3$). Most preferably, the C-terminal is amidated ("—$CONH_2$"), unless linked via the C-terminal to another peptide/fragment via a linker. Most preferably, the N-terminal comprises a free amino group ("$NH_2$"). In a highly preferred embodiment, the present disclosure relates to a peptide for use in the treatment of obesity, wherein said peptide comprises 16 amino acid residues and further wherein the peptide comprises a fragment with SEQ ID NO:1 (AQFHRHKQLIRFLKRA). In view of the fact that SEQ ID NO:1 has 16 amino acids, it should be understood from the wording "comprising" that the peptide may be e.g. lipidated and/or contain post-translational modifications commonly used in the art.

In another highly preferred embodiment, the present disclosure relates to a peptide for use in the treatment of obesity, wherein said peptide consists of SEQ ID NO:1 (AQFHRHKQLIRFLKRA) or a variant of SEQ ID NO:1 (AQFHRHKQLIRFLKRA) having one, two, or three amino acid substitutions.

In yet a highly preferred embodiment, the present disclosure relates to a peptide for use in the treatment of obesity, wherein said peptide is a peptide consisting of Ac-AQFHRHKQLIRFLKRA (SEQ ID NO:2).

In a most preferred embodiment, the present disclosure relates to a peptide for use in the treatment of obesity, wherein said peptide is a peptide consisting of AQFHRHKQLIRFLKRA (SEQ ID NO:1).

The peptides according to the invention are agonists on type I IL-4R and preferably antagonists on type II IL-4R. The agonists may be either super agonists, full agonists or partial agonists.

The peptides according of the invention may form part of a multimer such as a dimer, trimer, or tetramer. Multimers, e.g. peptide dendrimers, incorporating the peptides of the present disclosure may also be used. Most preferably, the peptide is in the form of a monomer or dimer, most preferably a dimer. Peptides according to the present disclosure may be covalently linked to form a multimer (e.g. a dimer)

by covalently connecting the peptides through various linkers (spacers), such as those commonly used in the art for fusion peptides or proteins.

In a second aspect of the present disclosure relates to a peptide or a pharmaceutically acceptable salt thereof for use in the treatment of obesity, wherein said peptide comprises two or more covalently linked peptide fragments derived from the α-helix C of IL-4.

Thus, in the second aspect, the present disclosure relates to a peptide or a pharmaceutically acceptable salt thereof for use in the treatment of obesity, wherein said peptide comprises two or more covalently linked fragments, wherein each fragment consists of 13 to 19 contiguous amino acid residues derived from the amino acid region $AA_{68}$-$AA_{97}$, preferably $AA_{68}$-$AA_{89}$, more preferably $AA_{71}$-$AA_{94}$ (i.e. the α-helix C of IL-4), even more preferably $AA_{71}$-$AA_{89}$, most preferably $AA_{71}$-$AA_{86}$, of interleukin-4 (SEQ ID NO:4), or a variant thereof having one, two, three, or four amino acid substitutions. In a preferred embodiment of the second aspect, each fragment consists of 14 to 18 contiguous amino acid residues derived from the amino acid region $AA_{68}$-$AA_{97}$, preferably $AA_{68}$-$AA_{89}$, more preferably $AA_{71}$-$AA_{94}$, even more preferably $AA_{71}$-$AA_{89}$, most preferably $AA_{71}$-$AA_{86}$, of interleukin-4 (SEQ ID NO:4), or is a variant thereof having one, two, three, or four amino acid substitutions. In a more preferred embodiment of the second aspect, each fragment consists of 15 to 17 contiguous amino acid residues derived from the amino acid region $AA_{68}$-$AA_{97}$, preferably $AA_{68}$-$AA_{89}$, more preferably $AA_{71}$-$AA_{94}$, even more preferably $AA_{71}$-$AA_{89}$, most preferably $AA_{71}$-$AA_{86}$, of interleukin-4 (SEQ ID NO:4), or is a variant thereof having one, two, three, or four amino acid substitutions. In an even more preferred embodiment of the second aspect, each fragment consists of 16 contiguous amino acid residues derived from the amino acid region $AA_{68}$-$AA_{89}$, more preferably $AA_{71}$-$AA_{94}$, even more preferably $AA_{71}$-$AA_{89}$, most preferably $AA_{71}$-$AA_{86}$, of interleukin-4 (SEQ ID NO:4), or is a variant thereof having one, two, three or four amino acid substitutions. In the above-mentioned embodiments of the second aspect, it is highly preferred that each fragment comprises the amino acid sequence AQFHRHKQLIRFLKRA (SEQ ID NO:1), or a variant of AQFHRHKQLIRFLKRA (SEQ ID NO:1) having one or two substitutions. Most preferably, the covalently linked fragments are identical. Most preferably, the peptide is a dimer (i.e. two covalently linked fragments).

In a preferred embodiment of the second aspect, the present disclosure relates to a peptide for use in the treatment of obesity, wherein said peptide comprises two or more covalently linked fragments, wherein each fragment consists of 13 to 19 amino acid residues, and further wherein said peptide comprises the amino acid sequence AQFHRHKQ-LIRFLKRA (SEQ ID NO: 1), or a variant of AQFHRHKQ-LIRFLKRA (SEQ ID NO:1) having one, two, or three amino acid substitutions and/or deletions.

In a more preferred embodiment of the second aspect, the present disclosure relates to a peptide for use in the treatment of obesity, wherein said peptide comprises two or more covalently linked fragments, wherein each fragment consists of 14 to 18 amino acid residues, and further wherein each fragment comprises the amino acid sequence AQFHRHKQ-LIRFLKRA (SEQ ID NO:1), or a variant of AQFHRHKQ-LIRFLKRA (SEQ ID NO:1) having one, two, or three amino acid substitutions and/or deletions.

In a yet more preferred embodiment of the second aspect, the present disclosure relates to a peptide for use in the treatment of obesity, wherein said peptide comprises two or more covalently linked fragments, wherein each fragment consists of 15 to 17 amino acid residues, and further wherein each fragment comprises the amino acid sequence AQFHRHKQLIRFLKRA (SEQ ID NO:1), or a variant of AQFHRHKQLIRFLKRA (SEQ ID NO:1) having one, two, or three amino acid substitutions and/or deletions.

In an even more preferred embodiment of the second aspect, the present disclosure relates to a peptide for use in the treatment of obesity, wherein said peptide comprises two or more covalently linked fragments, wherein each fragment consists of 16 amino acid residues, and further wherein the peptide comprises SEQ ID NO:1 (AQFHRHKQ-LIRFLKRA) or a variant of SEQ ID NO:1 (AQFHRHKQ-LIRFLKRA) having one, two, or three amino acid substitutions.

In any of the above-mentioned embodiments of the second aspect, the variant preferably has two amino acid substitutions and/or deletions, even more preferably one amino acid substitution or deletion. In any of the above-mentioned embodiments of the second aspect, the peptide most preferably comprises two covalently linked fragments (i.e. a dimer), wherein each fragment consists of the same sequence.

In a most preferred embodiment of the second aspect, the present invention relates to a peptide for use in the treatment of obesity, wherein said peptide has the structure of Formula (I):

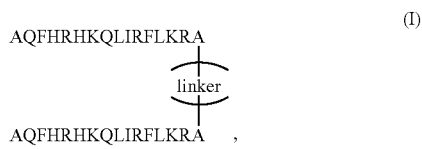

(I)

or is variant thereof having one, or two amino acid substitutions in each peptide fragment.

Each fragment of SEQ ID NO:1 (i.e. AQFHRHKQ-LIRFLKRA) in the dimeric peptide of formula (I) is covalently connected through a linker at their C-terminal.

In another most preferred embodiment of the second aspect, the present disclosure relates to a peptide for use in the treatment of obesity, wherein said peptide is a dimer of SEQ ID NO:1 connected through a linker (lysine-beta-alanine) as shown in the structure below (compound A):

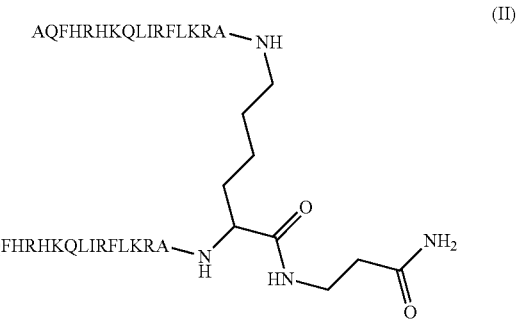

(II)

In another embodiment of the second aspect, the present invention relates to a peptide for use in the treatment of obesity, wherein said peptide forms part of a tetrameric dendrimer comprising four copies of SEQ ID NO:1 and/or SEQ ID NO:2, or a variant thereof comprising one, two, or three amino acid substitutions. In another preferred embodiment, the peptide is a dimeric dendrimer comprising two copies of SEQ ID NO:1, or a variant thereof comprising one, two, or three amino acid substitutions, or two copies of SEQ ID NO:2, or a variant thereof comprising one, two, or three amino acid substitutions. In another embodiment, the peptide is a tetrameric dendrimer comprising four copies of SEQ ID NO:1, or a variant thereof comprising one, two, or three amino acid substitutions, or four copies of SEQ ID NO:2, or a variant thereof comprising one, two, or three amino acid substitutions.

In a third aspect, the present disclosure relates to a pharmaceutical composition for use in the treatment of obesity, wherein said pharmaceutical composition comprises one or more peptides according to the aspects and embodiments disclosed herein. The pharmaceutical composition may comprise acceptable pharmaceutical carriers and optionally one or more excipients. The pharmaceutical composition (i.e. formulation) includes but are not limited to tablets, pills, capsules, emulsions, suspensions, sustained release formulations, solutions, or freeze-dried powder intended for dissolution prior to administration. In some embodiments, the formulation may be a depot formulation providing slow release. It should be appreciated that different routes of administration may be used depending on the choice of formulation and chemical and/or metabolic stability of the polypeptides. Such administration routes may include but are not limited to oral administration, parenteral administration (intravenous (IV), subcutaneous (SC), intradermal (ID) and intramuscular (IM)), or inhalation. In a preferred embodiment of the invention, the administration route is parental administration. In an even more preferred embodiment, the administration route is subcutaneous.

In a fourth aspect, the present disclosure relates to a method for treatment of obesity, the method comprising administering an effective amount of a peptide to an individual in need thereof according to any of the aspects and embodiments disclosed herein.

EXAMPLES

Example 1: Effect of an IL-4 Derived Peptide on Body Weight

Material and Methods

Animals 30 female mice (BKS.Cg-Dock7m+/+Leptin db/db BLKS, 5 weeks of age) were transferred to the Gubra Research animal unit in Denmark. Throughout the habituation and study period, the animals were housed in a light-, temperature-, and -humidity-controlled room with free access to food and water. All animal experiments were conducted in accordance with Gubra bioethical guidelines, which are fully compliant with internationally accepted principles for the care and use of laboratory animals. The body weight of the animals was recorded at the start of the study (baseline), on day 13, day 27, day 34, day 43, day 60 and day 77 (termination of study).

Compounds

Compound A was prepared using standard solid phase peptide synthesis (SPPS) procedures. Compound A was provided by Phlogo ApS, Copenhagen, Denmark (10 mg/ml miliQ water diluted to the dose formulations). Vehicle was miliQ:PBS 1:5.

In Vivo Procedures

The mice were randomized into a vehicle group (n=15) and a 10 mg/kg Compound A (n=15). The compound as well as the vehicle was administered subcutaneously once daily. On day 27, the dose was lowered to 5 mg/kg Compound A (n=15), and on day 43, the dose was lowered to 2.5 mg/kg Compound A (n=15).

Results

As compared to vehicle, the tested Compound A significantly decreased the weight in the treatment group receiving compound A. The weight results (mean values) are shown below in Table 1.

TABLE 1

| Animal | Weight at baseline (g) | Weight at day 77 (g) | Δ Weight (g) |
| --- | --- | --- | --- |
| Treatment group | | | |
| 1 | 48.00 | 59.40 | 11.40 |
| 2 | 49.20 | 52.40 | 3.20 |
| 3 | 50.50 | 49.20 | −1.30 |
| 4 | 53.40 | 54.30 | 0.90 |
| 5 | 48.00 | 49.40 | 1.40 |
| 6 | 52.50 | 54.30 | 1.80 |
| 7 | 48.90 | 47.30 | −1.60 |
| 8 | 41.10 | 48.40 | 7.30 |
| 9 | 48.10 | 52.50 | 4.40 |
| 10 | 54.60 | 59.10 | 4.50 |
| 11 | 44.90 | 47.60 | 2.70 |
| 12 | 39.40 | 37.50 | −1.90 |
| 13 | 49.30 | 57.30 | 8.00 |
| 14 | 47.60 | 51.80 | 4.20 |
| 15 | 46.90 | 58.10 | 11.20 |
| Mean | 45.15 | 48.66 | 3.51 |
| Placebo group | | | |
| 16 | 51.60 | 60.30 | 8.70 |
| 17 | 47.40 | 50.40 | 3.00 |
| 18 | 47.20 | 54.50 | 7.30 |
| 19 | 49.60 | 56.00 | 6.40 |
| 20 | 46.20 | 48.30 | 2.10 |
| 21 | 51.80 | 56.30 | 4.50 |
| 22 | 52.20 | 63.50 | 11.30 |
| 23 | 48.60 | 52.30 | 3.70 |
| 24 | 48.60 | 55.10 | 6.50 |
| 25 | 48.20 | 46.60 | −1.60 |
| 26 | 43.80 | 50.50 | 6.70 |
| 27 | 54.60 | 62.00 | 7.40 |
| 28 | 48.20 | 50.70 | 2.50 |
| 29 | 41.90 | 51.80 | 9.90 |
| 30 | 38.20 | 51.90 | 13.70 |
| Mean | 44.88 | 50.64 | 5.76 |

Discussion

Interestingly, the weight gain is significantly smaller in the treatment group compared to the placebo group. The animals in the placebo group in average increased their weight by 5.76 g (12.8%) during the study period. On the contrary, the treatment group only increased their weight by 3.51 g (7.8%). Thus, compound A (SEQ ID NO:1) decreased the weight gain.

Sequence overview

SEQ ID NO: 1
AQFHRHKQLIRFLKRA

SEQ ID NO:2
Ac-AQFHRHKQLIRFLKRA

-continued

Sequence overview

SEQ ID NO: 3 (IL-4 peptide including signal peptide, 153 amino acids)
MGLTSQLLPP LFFLLACAGN FVHGHKCDIT LQEIIKTLNS
LTEQKTLCTE LTVTDIFAAS KNTTEKETFC RAATVLRQFY
SHHEKDTRCL GATAQQFHRH KQLIRFLKRL DRNLWGLAGL
NSCPVKEANQ STLENFLERL KTIMREKYSK CSS SEQ ID NO: 4 (IL-4 peptide without signal peptide, 129 amino acids)
HKCDIT LQEIIKTLNS LTEQKTLCTE LTVTDIFAAS KNTTEKETFC
RAATVLRQFY SHHEKDTRCL GATAQQFHRH KQLIRFLKRL
DRNLWGLAGL NSCPVKEANQ STLENFLERL KTIMREKYSK CSS

REFERENCES

Roglic, G. World Health Organization. (2016). Global report on diabetes. ISBN 9789241565257.

Abdelaal M. et al. Morbidity and mortality associated with obesity. Ann Transl Med. 2017 April; 5(7): 161, p. 112-12.

Klementiev B. et al. Antiinflammatory properties of a peptide derived from interleukin-4. Cytokine, Vol. 64, No. 1, 10.2013, p. 112-21.

Items

1. A peptide or a pharmaceutically acceptable salt thereof for use in the treatment of obesity, wherein the peptide comprises a fragment consisting of 13 to 19 contiguous amino acid residues derived from the amino acid region $AA_{68}$-$AA_{97}$, preferably $AA_{68}$-$AA_{89}$ of interleukin-4 (SEQ ID NO:4), or a variant thereof having one, two, three, or four amino acid substitutions.

2. A peptide for use according to any of the preceding items, wherein said peptide comprises a fragment consisting of 14 to 18 contiguous amino acid residues derived from the amino acid region $AA_{68}$-$AA_{97}$, preferably $AA_{68}$-$AA_{89}$ of interleukin-4 (SEQ ID NO:4), or a variant thereof having one, two, three or four amino acid substitutions.

3. A peptide for use according to any of the preceding items, wherein said peptide comprises a fragment consisting of 15 to 17 contiguous amino acid residues derived from the amino acid region $AA_{68}$-$AA_{97}$, preferably $AA_{68}$-$AA_{89}$ of interleukin-4 (SEQ ID NO:4), or a variant thereof having one, two, three, or four amino acid substitutions.

4. A peptide for use according to any of the preceding items, wherein said peptide comprises a fragment consisting of 16 contiguous amino acid residues derived from the amino acid region $AA_{68}$-$AA_{97}$, preferably $AA_{68}$-$AA_{89}$ of interleukin-4 (SEQ ID NO:4), or a variant thereof having one, two, three, or four amino acid substitutions.

5. A peptide for use according to any of the preceding items, wherein the amino acid residues are derived from the amino acid region $AA_{71}$-$AA_{94}$, (i.e. the α-helix C of IL-4), preferably $AA_{71}$-$AA_{89}$, most preferably $AA_{71}$-$AA_{86}$.

6. A peptide for use according to any of the preceding items, wherein said peptide comprises a fragment consisting of the amino acid sequence AQFHRHKQLIRFLKRA (SEQ ID NO:1), or a variant thereof having one or two substitutions.

7. A peptide for use according to any of the preceding items, wherein said peptide comprises two or more identical fragments covalently linked through a linker.

8. A peptide or a pharmaceutically acceptable salt thereof for use in the treatment of obesity, wherein the peptide is dimer comprising two fragments, each fragment consisting of 13 to 19 contiguous amino acid residues derived from the amino acid region $AA_{71}$-$AA_{94}$, of interleukin-4 (SEQ ID NO:4) (i.e. the α-helix C of IL-4), or a variant thereof having one, two, three, or four amino acid substitutions, wherein each fragment is covalently linked through a linker.

9. A peptide for use according to item 8, wherein the amino acid residues are derived from the amino acid region $AA_{71}$-$AA_{89}$, most preferably $AA_{71}$-$AA_{86}$.

10. A peptide for use according to any of items 8-9, wherein each fragment consists of 14 to 18 contiguous amino acid residues, preferably 15 to 17 contiguous amino acid residues, most preferably 16 amino acid residues.

11. A peptide for use according to any of items 8-10, wherein said peptide comprises two identical fragments.

12. A peptide for use according to items any of the preceding items, wherein has the structure of the Formula (I):

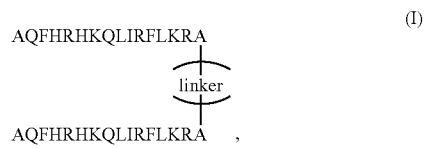

(I)

or is a variant thereof having one or two substitutions in each peptide fragment.

13. A peptide according to any of the preceding items, wherein the peptide is an agonist on type I IL-4R and an antagonist on type II IL-4R.

SEQUENCE LISTING

```
Sequence total quantity: 4
SEQ ID NO: 1            moltype = AA  length = 16
FEATURE                 Location/Qualifiers
source                  1..16
                        mol_type = protein
                        organism = synthetic construct
SEQUENCE: 1
AQFHRHKQLI RFLKRA                                                     16

SEQ ID NO: 2            moltype = AA  length = 16
FEATURE                 Location/Qualifiers
source                  1..16
                        mol_type = protein
                        organism = synthetic construct
SITE                    1
                        note = X = Ac-A (i.e. N-acetyl-L-alanine)
SEQUENCE: 2
XQFHRHKQLI RFLKRA                                                     16

SEQ ID NO: 3            moltype = AA  length = 153
FEATURE                 Location/Qualifiers
source                  1..153
                        mol_type = protein
                        organism = Homo sapiens
SEQUENCE: 3
MGLTSQLLPP LFFLLACAGN FVHGHKCDIT LQEIIKTLNS LTEQKTLCTE LTVTDIFAAS      60
KNTTEKETFC RAATVLRQFY SHHEKDTRCL GATAQQFHRH KQLIRFLKRL DRNLWGLAGL     120
NSCPVKEANQ STLENFLERL KTIMREKYSK CSS                                  153

SEQ ID NO: 4            moltype = AA  length = 129
FEATURE                 Location/Qualifiers
source                  1..129
                        mol_type = protein
                        organism = Homo sapiens
SEQUENCE: 4
HKCDITLQEI IKTLNSLTEQ KTLCTELTVT DIFAASKNTT EKETFCRAAT VLRQFYSHHE      60
KDTRCLGATA QQFHRHKQLI RFLKRLDRNL WGLAGLNSCP VKEANQSTLE NFLERLKTIM     120
REKYSKCSS                                                             129
```

The invention claimed is:
1. A method for the treatment of obesity, said method comprising administering a therapeutically effective amount of a peptide or a pharmaceutically acceptable salt thereof, wherein the peptide comprises the amino acid sequence AQFHRHKQLIRFLKRA (SEQ ID NO: 1).
2. The method of claim 1, wherein the peptide has the structure of the Formula (I):
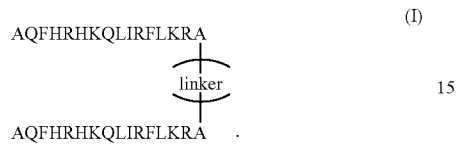
(I)
* * * * *